United States Patent
Vestergaard Frandsen et al.

(10) Patent No.: US 8,906,400 B2
(45) Date of Patent: Dec. 9, 2014

(54) INSECTICIDAL POLYMER MATRIX COMPRISING PBO AND DM

(75) Inventors: Mikkel Vestergaard Frandsen, Lausanne (CH); Michael Stanley Pedersen, Vaud (CH); Matthieu Zellweger, Geneva (CH); Sebastien Gouin, Ha Noi (VN); Sicco Dirk Roorda, Pully (CH); Thi Quynh Chi Phan, Hanoi (VN)

(73) Assignee: Vestergaard Frandsen SA, Lausanne (CH)

( * ) Notice: Subject to any disclaimer, the term of this patent is extended or adjusted under 35 U.S.C. 154(b) by 283 days.

(21) Appl. No.: 13/057,776

(22) PCT Filed: Jul. 23, 2009

(86) PCT No.: PCT/DK2009/050188
§ 371 (c)(1),
(2), (4) Date: Mar. 25, 2011

(87) PCT Pub. No.: WO2010/015257
PCT Pub. Date: Feb. 11, 2010

(65) Prior Publication Data
US 2012/0121681 A1 May 17, 2012

(30) Foreign Application Priority Data
Aug. 6, 2008 (DK) .................. 2008 01073

(51) Int. Cl.
*A01N 25/34* (2006.01)
*A01N 25/08* (2006.01)
*A01N 53/00* (2006.01)

(52) U.S. Cl.
CPC ...................... *A01N 53/00* (2013.01)
USPC ............................ 424/411; 424/409; 514/464

(58) Field of Classification Search
None
See application file for complete search history.

(56) References Cited

U.S. PATENT DOCUMENTS 6,881,248 B2 * 4/2005 Lee et al. .................. 106/18.32
2004/0134377 A1 7/2004 Lee

FOREIGN PATENT DOCUMENTS

| AU | B-47404/93 | 3/1994 |
| WO | 02/43487 | 6/2002 |
| WO | 03034823 | 5/2003 |
| WO | 2006/111553 | 10/2006 |
| WO | 2008/004711 | 1/2008 |
| WO | 2008/032842 | 3/2008 |
| WO | 2008/032844 | 3/2008 |
| WO | 2010/046348 | 4/2010 |

OTHER PUBLICATIONS

Schuerman et al. J. Chem. Educ., 1989, 66 (4), p. 327.*
Fakoorziba, M.R. et al.; Synergist efficacy of piperonyl butoxide with deltamethrin as pyrethroid insecticide on *Culex tritaeniorhynchus* (Diptera: Culicidae) and other mosquitoe species; Chemical Abstract; Oct. 9, 2013, pp. 1, 2, 150:368119.

* cited by examiner

*Primary Examiner* — Abigail Fisher
*Assistant Examiner* — Daniel L Branson
(74) *Attorney, Agent, or Firm* — James Creighton Wray

(57) ABSTRACT

An insecticidal polymer matrix containing Piperonyl Butoxide (PBO) and deltamethrin (DM), wherein the ratio between the content of PBO and the content of DM in terms of weight is higher than 3.

16 Claims, 5 Drawing Sheets

INSECTICIDAL POLYMER MATRIX COMPRISING PBO AND DM

This application claims the benefit of Danish Application No. PA 2008, 01073 filed Aug. 6, 2008 and PCT/DK2009/050188 filed Jul. 23, 2009, and the amended sheets from the IPEA, which are hereby incorporated by reference in their entirety as if fully set forth herein.

FIELD OF THE INVENTION

The present invention relates to an insecticidal polymer matrix comprising piperonyl butoxide and deltamethrin.

BACKGROUND OF THE INVENTION

In connection with insecticide control, it is well known that insecticides can be integrated in polymer material in order to prevent insects to work their way through the material. However, when it comes to the control of release rates of insecticides in a polymer matrix, this is regarded as a difficult issue, because a release that is too rapid exhausts the matrix quickly with regard to insecticidal effect, and a too slow release does not have the desired efficiency or suitable regeneration properties in case the insecticide falls off or is removed, for instance, by washing.

For crop sheets, as disclosed in U.S. Pat. No. 4,888,174, it is known to mix LDPE with other polymers in order to reduce the migration speed. This is in line with the disclosure of International Patent Application WO 02/34487, stating that "the selection of the polymers depends on the desired release rate", where the disclosure proposes a pesticide-retaining layer of LDPE (low density polyethylene) bonded to a layer of HDPE (high density polyethylene), where the HDPE layer prevents a too fast release of the insecticide.

For cables, it is known from U.S. Pat. No. 4,680,328 to extrude insecticidal polymer blends with LDPE, HDPE and LLDPE (linear low density polyethylene) and a preferred insecticide halopyridyl phosphate.

Apart from the difficulty of achieving a suitable migration speed of insecticide in polymer matrices, the combination of an insecticide, for example DM (Deltamethrin), and a synergist, for example PBO (piperonyl butoxide), incorporated in a polymer matrix implies additional challenges. Despite the fact that incorporation of a pyrethroid and PBO has been reported in connection with pet collars, for example in International patent application WO 00/40084 or WO 06/127407, the migration speed for long lasting insecticidal nets (LLIN) or fabrics is still an unresolved problem in practice. This is due to the fact that several parameters have to be fitted together to yield a product that is satisfactory. The parameters have to be found such that, firstly, the insecticidal dose on the surface of the material should be sufficiently high for killing insects, secondly, the release should last for more than a year in the case of LLIN, and should allow regeneration of the net's activity in case of washing of the net, and thirdly, the overall content of the insecticide and synergist should be low in order to keep the cost for LLIN at a minimum, as well as to minimize the potential exposure of an end-user to the active ingredients contained in the net. The latter are important factors, because the largest markets for LLIN are regions with low income, and the primary end-users are infants and young children.

Especially, for insecticidal polymer matrices containing DM and PBO, the optimal ratio between the content of DM relative to the content of PBO in terms of weight is still an open questions.

International patent application WO 2006/111553 discloses microcapsules with a solution of an insecticide, for example DM, and a synergist, for example PBO, in an aqueous suspension inside a polyurea capsule. The ingredients of the microcapsule are released due to breakage of the microcapsule wall when it dries after spraying. The background for this disclosure is the assumption that release of the insecticide should be several hours delayed as compared to the release of the synergist. In the disclosed Example 5, the amount of synergist PBO relatively to the insecticide DM is a factor of 2 in the premix A. As shown in FIG. 1, this premix is then surrounded by an emulsion containing a premix B containing 81% PBO. When used in connection with FIG. 2 of WO 2006/111553, the blend of Premix A and premix B with 5.9% DM and 23.9% PBO yields a ratio of 4.1 between PBO and DM which is further surrounded by premix B containing PBO. Although stating precise figures for containment of PBO and DM in an aqueous suspension inside a microcapsule for delayed release of DM relative to PBO, this disclosure does not give any hint as to the content of PBO relative to DM in a polymer matrix, for example a polyethylene matrix, where the insect shall be exposed to PBO and DM simultaneously by DM and PBO migrated to the surface of the matrix.

OBJECT OF THE INVENTION

Therefore, it is the object of the invention to provide an insecticidal polymer matrix with DM and PBO, where the ratio between DM and PBO is optimised.

DESCRIPTION OF THE INVENTION

This purpose is achieved with an insecticidal polymer matrix made of a material containing Piperonyl Butoxide (PBO) and deltamethrin (DM) as part of the material for migration of the PBO and the DM from inside the material to the surface of the matrix. The PBO content is higher than 3 times the content of the DM in the polymer matrix in terms of weight. Preferably, the PBO content is higher than 4 times or 5 times the content of the DM in the polymer matrix, for example between 5 and 10 times or between 8 and 10. The above mentioned minimum ratios between the PBO and the pyrethroid are much higher than the ratio of 2 as disclosed in WO 00/40084.

The invention is highly suitable for producing insecticidal fibres for LLIN and other insecticidal fabrics.

The polymer may advantageously be a polyolefin, for example polypropylene or polyethylene.

International patent application WO 2008/004711 discloses an insecticidal resin containing HDPE and LDPE. Deltamethrin is one of the possibilities of insecticides, however, no relation is stated for the ratio between HDPE and LDPE in this resin with deltamethrin. A ratio of 12.1 is implicitly stated in a single example for an HDPE/LDPE matrix containing 87.23% HDPE and 7.2% LDPE, permethrin, fine silica powder and a number of other ingredients. Although permethrin is also a pythroid, this ratio of 12.1 contains no information about advantageous ratios of HDPE/LDPE for deltamethrin (DM). This is so, because DM has a much higher molecular weight than permethrin, which influences the diffusion coefficient;

DM has a higher polarity than permethrin which results in DM having a lower affinity in the non-polar PE; and DM has a vapour pressure an order of magnitude lower than permethrin.

Furthermore, the example states the content of fine silica powder, zinc stearate, and other ingredients affecting the migration rate of permethrin. In addition, the effective insecticidal amount needed on the surface of the substrate, is generally different for the two insecticides permethrin and DM. Using this above information about the difference between DM and permethrin, the conclusion is that the ratio should be much smaller than the stated 12.1 for permethrin. However, it is desirable to have a more precise indication for the ratio between HDPE and LDPE in an insecticidal matrix useful in connection with DM.

Experimentally, there have been achieved good results for polyethylene matrices containing HDPE and LDPE, wherein the ratio of the contents of HDPE and LDPE is between 3 and 30, preferably between 5 and 20, for example between 5 and 11 or between 8 and 10.

Having regard to the interval of between 5 and 20 when containing DM, this result is surprising relative to the disclosure of a ratio of 12.1 for permethrin in International patent application WO 2008/004711, because one should expect the optimal ratio for DM be substantially different from 12.1, for example a ratio equal to a value around 2 or less due to the entirely different nature of DM, which is in solid form with entirely different parameters than the liquid permethrin.

The argument becomes more illustrative when using percentages. A ratio of 5 in a HDPE/LDPE matrix without other ingredients corresponds to 83% HDPE and 17% HDPE if no other ingredients are included in the matrix, and a ratio of 20 corresponds to 95% HDPE and 5% LDPE. Thus, the apparent broad interval of 5 to 20 corresponds to the relatively narrow interval of 83% to 95%. Having regard to the entire different nature of permethrin, one would expect the advantageous content of HDPE in the case of deltamethrin be much smaller than the than the 87.23% as disclosed for permethrin in WO 2008/004711. However, surprisingly, this is not the case.

As experiments have shown, the amount of LDPE in a polymer matrix with HDPE should not be too high, in order to assure an optimal migration rate of the PBO and the DM, whilst concomitantly achieving optimal mechanical properties of the polymer matrix. In this case, both substances migrate to the surface of the material, preferably a mosquito net, and expose the insect to PBO and DM instantaneously. This is a different strategy than for the micro capsules in the above mentioned International patent application WO 2006/111553 with a sequential exposure of PBO followed by DM.

Though, the two polymers HDPE and LDPE may be mixed with other polymers, experiments did show good results with only these two polymers constituting the polymer matrix. Also, preferably, the matrix is free from fine silica powder, or zinc stearate, or both of them in contrast to the matrix as disclosed in the above mentioned WO 2008/004711.

The surface content of PBO and DM on the surface of a polymer matrix depends on the migration rate of PBO and DM in the polymer but also on the thickness of the polymer substrate (i.e. the distance to the surface). The migration rate is influenced by, amongst other factors, the proportion of amorphous phase in the polymer (i.e. the percentage of crystallinity), the diffusion coefficient, which, in turn, is affected by the temperature and the degree of affinity between the additives and the polymer. Therefore, the surface content of DM and PBO at any moment in time is determined by a combination of various thermodynamic effects but also by the shape of the polymeric substrate being in the form of a yarn, a foil, or a bulk product.

The above ratios were verified as being especially useful for an insecticidal matrix in the form of a fully drawn monofilament yarn with a diameter of between 0.05 mm and 0.3 mm, preferably between 0.1 mm and 0.15 mm. Especially, the HDPE and LDPE ratio of between 5 and 11, 5 and 10, or between 8 and 10, was suitable for such filaments. However, the above figures are also useful for multifilaments having a linear density in the same range.

The content of deltamethrin, preferably, is less than 1.5%, more preferably less than 1%, of the weight of the polymer matrix.

A useful amount of DM in a matrix according to the invention is between 1 g and 6 g per kg polymer, for example, between 1 g and 5 g or between 2 g and 6 g or between 3 g and 5 g per kg polymer.

A preferred combination of parameters is the following,
the insecticidal matrix is in the form of a monofilament, preferably fully drawn, with a diameter of between 0.05 mm and 0.30 mm, or an insecticidal matrix in the form of monofilaments of the type between 50 and 100 Denier,
the weight content of DM is between 2 g and 6 g, for example between 3 g and 5 g, per kg polymer,
the weight content of PBO is more than 3 times, or rather more than 5 times, the weight content of the DM.

Another preferred combination is
the insecticidal matrix is in the form of a monofilament, preferably fully drawn, with a diameter of between 0.05 mm and 0.30 mm, or an insecticidal matrix in the form of monofilaments of the type between 50 and 100 Denier,
the ratio between the content of HDPE relative to the content of LDPE in the matrix is between 8 and 10, for example the content of LDPE is between 9% and 11%;
the weight content of DM is between 2 g and 6 g, for example between 3 g and 5 g, per kg polymer,
the weight content of PBO is more than 3 times, or rather more than 5 times, the weight content of the DM.

A preferred combination of parameters were the following,
the insecticidal matrix is in the form of a monofilament, preferably fully drawn, with a diameter of between 0.10 mm and 0.15 mm, or an insecticidal matrix in the form of monofilaments of the type between 50 and 100 Denier,
the ratio between the content of HDPE relative to the content of LDPE in the matrix is between 8 and 10, for example the content of LDPE is between 9% and 11%;
the weight content of DM is between 3 g and 5 g per kg polymer,
the weight content of PBO is between 5 and 7 times the weight content of the DM.

At this point, it should be emphasized that the content of DM is in the sub-percent range and the content of PBO is in the range of a few % only, whereas in International application WO 00/40084 the content of Pyrethroid is in the range of up to 10% and the content of PBO is in the range up to 20%. By including vast amounts of insecticide and synergist in a matrix, high insecticidal efficiency and also relatively long lasting effect can, indeed, be achieved. However, for LLIN, this must withstand the additional constraint of regeneration of insecticidal activity after washing in an interval that is relevant for the end product, typically less than seven days. Furthermore, the risk to end users and the production costs should be low, which requires an as low content as possible, though still enough for sufficient long lasting effect and multiple regenerations following repeated washings at regular intervals.

A highly preferred use of the filament matrix according to the invention is a monofilament yarn as part of a woven net, especially bed nets against mosquitoes. For bed nets, the entire net may be made of such insecticidal matrices according to the invention, but in some cases, it is preferred that only the roof is made thereof. The side walls could then be made of polymer containing DM but not PBO, for example a polyethylene matrix with DM. Alternatively, the side walls are made of another material, for example polyethylene terephthalate (PET), also called polyester (PES).

One of the ways to slow down chemical or photochemical degradation of PBO and DM on the surface of the matrix uses an antioxidant distributed, preferably homogenously distributed, in the polymeric substrate. Such antioxidants is used to decompose as fast as possible any reactive species, for example radicals and peroxides, formed with time on order to prevent reaction with and changing of the chemical nature of DM or PBO in such a way that their bioactivities is detrimentally affected.

In addition, special migration promotors or inhibitors may be used to adjust the migration speed. For example, some promotors or inhibitors may work more or less on DM than on PBO, by which the migration speed of these two components can be adjusted relatively.

The matrix according to the invention is primarily intended for extrusion, however, it may as well be used in moulding processes. Thus, the DM and the PBO are incorporated into the molten polymer.

Other ingredients for a matrix according to the invention are found among UV protectors, plasticizers, colorants, preservatives, detergents, fillers, impact modifiers, anti-fogging agents, blowing agents, clarifiers, nucleating agents, coupling agents, conductivity-enhancing agents to prevent static electricity, stabilizers, for example, carbon and oxygen radical scavengers, flame retardants, mould release agents, optical brighteners, spreading agents, antiblocking agents, foam-forming agents, anti-soiling agents, thickeners, further biocides, wetting agents, plasticizers adhesive or anti-adhesive agents, fragrance, pigments and dyestuffs and other liquids including water or organic solvents.

Apart from the incorporation of DM and PBO in the matrix, the matrix may be coated with other insecticidal agents, for example Carbamates or Organophosphates. This can be used as a measure against insecticidal resistance. However, in this case, it should be assured that the coating is configured for migration of the DM and PBO through the coating.

Apart from using the matrix according to the invention for bednets and fabrics, the matrix may also be used for tarpaulins, foils, flat yarns and bulk material. Such different materials may be combined by different kind of bonding techniques or sewing techniques. Also, materials with an insecticidal polymer matrix according to the invention may be combined with materials containing other insecticides. For example, a net or fabric with a polymer matrix according to the invention may be combined with a different net, fabric, foil, flat yarn or tarpaulin containing a different insecticide in order to combat insecticidal resistance.

The extrusion should be relatively mild, with a temperature lower than 240° C., and with minimal residence time, water quenching of the yarns, and in-line drawing of the yarn to a draw ratio of 5 to 10, rather 8 to 10, thus, achieving the crystallinity of the yarn/matrix associated with the state of "fully drawn yarn" and the desired migration rate and as well as other suitable physical properties.

Generally, it seems that an advantage over the prior art is achieved, if an insecticidal polymer matrix is selected with HDPE (high density polyethylene), LDPE (low density polyethylene), wherein the ratio of the contents of HDPE and LDPE is between 3 and 30, preferably between 5 and 20 or between 5 and 11 or between 8 and 10. Such a matrix is advantageous also for other insecticides than DM and other synergists than PBO. However, the insecticide, and optionally the synergist, should be able to migrate in the matrix.

For mosquito nets, for example with fibres of 75 or 100 Denier, a non limiting appropriate content of DM is larger than 1 g/kg, preferably larger than or at least 2 g/kg. Optionally, the content of DM is lower than 5 g/kg, preferably at most or lower than 4 g/kg. Thus, an interval of between 1 and 5 g/kg or, preferably, between 2 and 4 g/kg has been experienced as a good interval for such fibres in mosquito nets.

Optionally, the end points of all stated intervals may be part of the intervals.

DESCRIPTION OF THE DRAWING

The invention will be explained in more detail with reference to the drawing, where.

DETAILED DESCRIPTION OF THE INVENTION

The path leading to the invention did comprise a number of intermediate steps, in as much as the solution, despite its simplicity is not straightforward.

In the teaching in the field of insecticidal nets, it has hitherto been assumed that PBO has to be transferred to the mosquito well in advance to the exposure to DM, because the PBO was believed to need a certain time in the mosquito before it temporarily breaks down the resistance mechanism. This is reflected in the above mentioned International patent application WO 2006/11155. As the degradation of PBO by sunlight/visible light creates radicals leading to a degradation of the DM, it has hitherto been believed that a provision of PBO and DM at the surface of the net at the same time and at the same position is a hinder for an efficient insecticidal net, because the time lapse between the necessary PBO exposure to the mosquito before the DM exposure leads to a degradation of the DM in the mean time. This implied a conclusion that a polymer having incorporated DM as well as PBO for migration to the surface of the material is not a proper material for insecticidal nets. It should be mentioned here that no LLIN with incorporated PBO and DM have found way to the market yet, despite a great demand for a feasible solution. Instead, encapsulation of synergist and insecticide together with an antioxidant into UV protected microcapsules has been proposed in U.S. Pat. No. 4,056,610 as one of the measures to overcome this problem.

Figure 1:
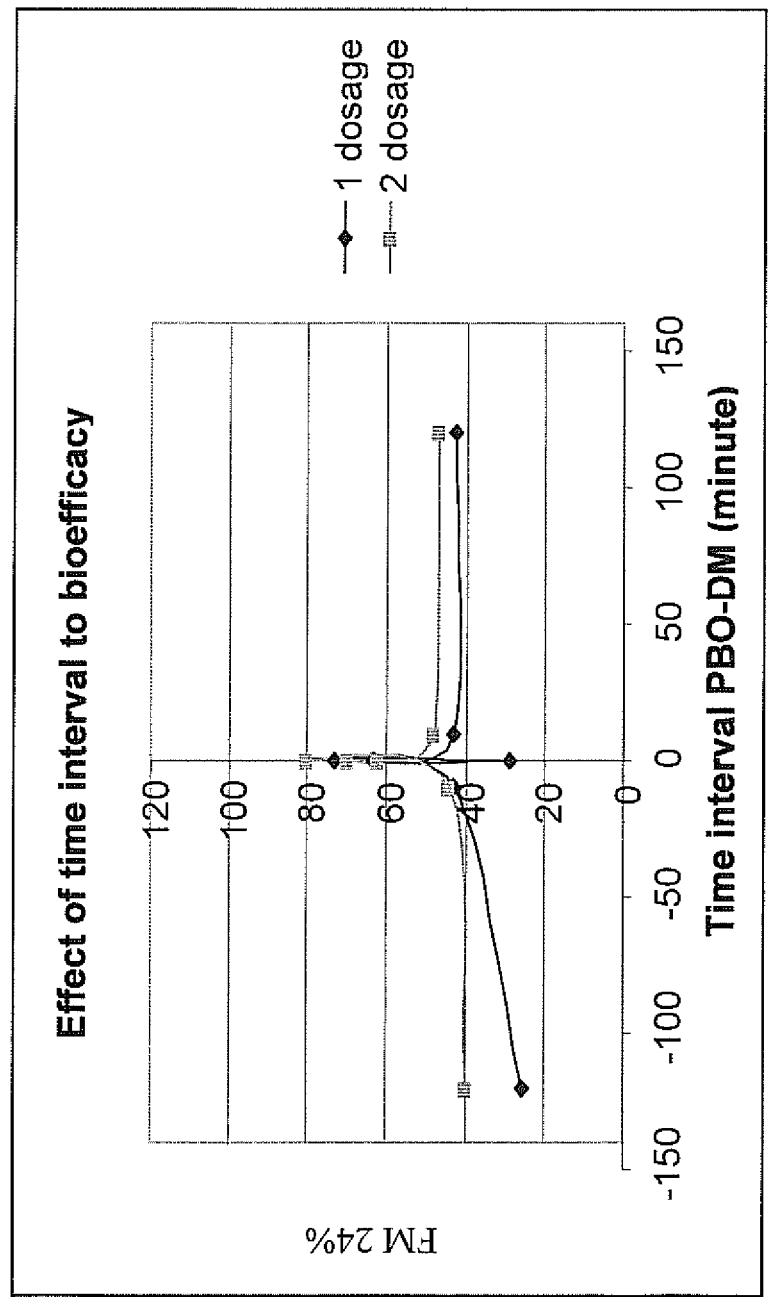
FIG. 1 illustrates the influence of time lag on the efficacy of PBO exposure and DM.

One of the corner stones of the invention is the fact that experiments revealed that the bioefficacy of PBO and DM treatment is highest when mosquitoes were exposed to PBO and DM simultaneously. As described above, this is against the teaching in the field of insecticidal nets. A proof for this is illustrated in FIG. 1, showing that for different dosages, there was a remarkable increase in efficacy when DM and PBO were provided to the mosquito at the same time.

Having recognised this, there was a new motivation for providing a polymer matrix containing PBO and DM, where both can be found on the surface of the matrix and migrate at a similar rate so as to replenish the surface after depletion (by washing, for instance) in order to expose insects to DM and PBO at the same time. As long as there is a steady release of these two substances, the efficacy against mosquitoes is optimal. Of course, this is compounded by the added constraint for LLINs that the said polymer matrix, once knitted into a netting material, should have suitable migration properties so that PBO and DM be regenerated at the surface of the yarn/fabric following washing.

The question then arises, which material should be chosen for the matrix. Studies revealed that polyester has a very slow migration rate, which was not sufficient to release enough DM and PBO through migration of polyester yarn of 100 Denier, even when used a multifilament with 35 filaments. HDPE had a release rate which was higher than for polyester, but not high enough for sufficient insecticidal efficacy or regeneration at a rate suitable for mosquito netting materials, despite good mechanical properties making it suitable for knitting into netting material. On the other hand, LDPE has a migration rate, which is far too high for a LLIN, and yarns made of pure LDPE have low mechanical properties that make them unsuitable for knitting into netting material. Thus, according to the invention, a mixture of LDPE and HDPE was envisaged, and it was found empirically, that for sufficient but also long lasting release of DM and PBO, a mixture of HDPE and LDPE was optimum, where the weight ratio between HDPE and LDPE was between 30 and 3 and rather between 20 and 5. The ratio depends on the thickness of the matrix. For monofilament yarns with a thickness of 0.06 mm, the HDPE/LDPE weight ratio was best between 15 and 25 and for yarns with a thickness of 0.25 mm, the ratio was best between 4 and 7. For yarn thickness in between these two numbers, the ratio may be interpolated. These parameters seem to give the said monofilament yarns adequate crystallinity at a given draw ratio and therefore an appropriate migration rate at the typical temperature these products are used.

In the experiments, no other polymers were introduced into the matrix. The above ratios corresponded in these experiments to a LDPE weight content of between 3.5% and 35% in the HDPE/LDPE matrix, whereas, however, the preferred content of LDPE in terms of weight was between 5% and 17%, better between 8% and 12%.

A successful monofilament yarn with a diameter of 0.10 mm to 0.15 mm, for example around 0.12 mm, the content of HDPE and LDPE in terms of weight was at a ratio between 8 and 10, rather around 9, corresponding to an LDPE content of around 10%, when no other polymers were introduced.

However, as it turned out, not only the ratio between the content of HDPE and LDPE could be used to optimise the yarn with respect to long lasting high efficiency. Also the content of the PBO content relative to the DM content proves to be crucial.

Figure 2:
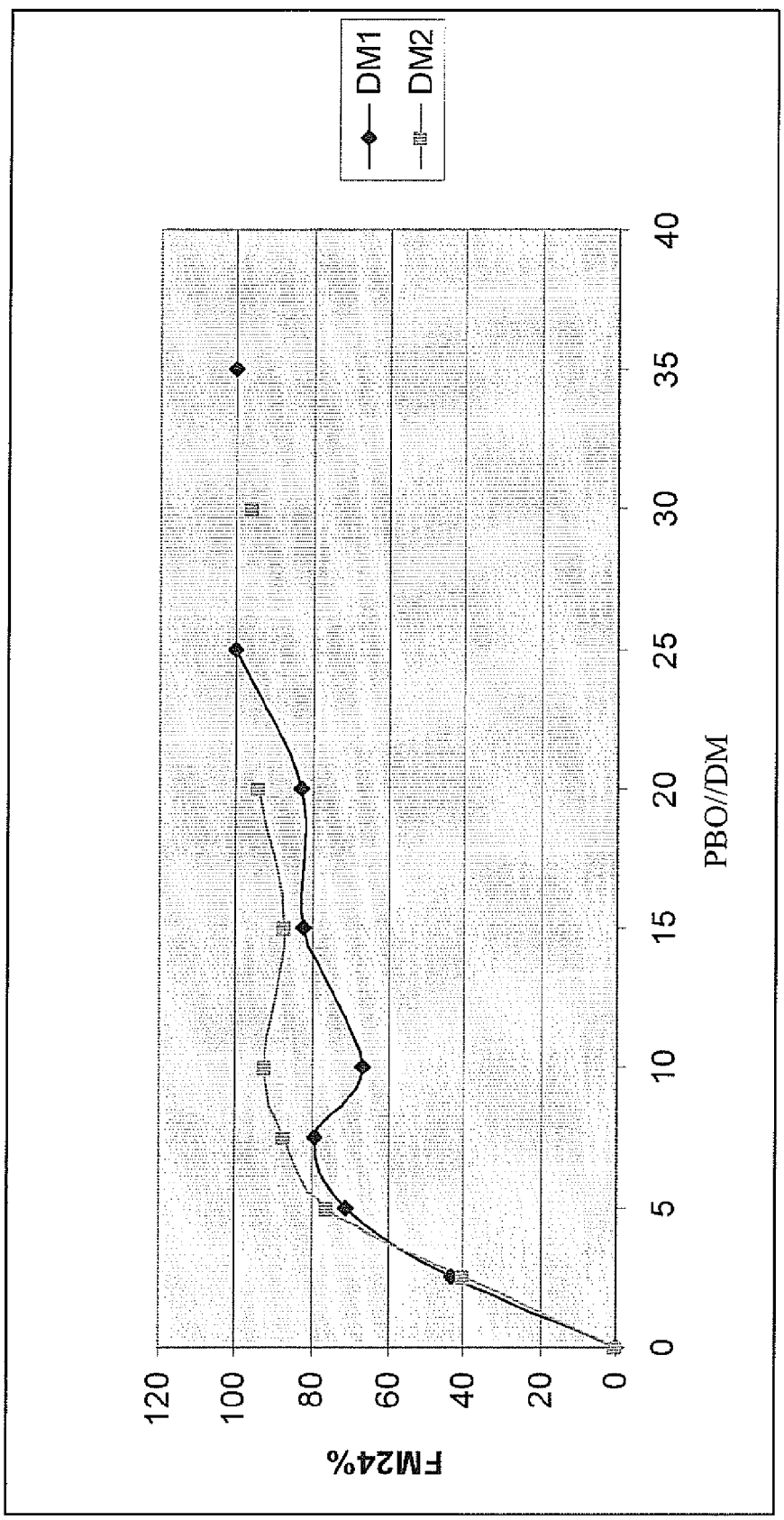
FIG. 2 illustrates the effect of the content ratio between PBO and DM.

In this connection, FIG. 2 shows the PBO/DM ratio as abscissa and a percentage Functional Mortality of resistant *Culex quinquefasciatus* as ordinate for two different DM dosages, namely dosage DM1=1.32 mg/m$^2$ and dosage DM2=1.76 mg/m$^2$ in a WHO cone test with a mixture of DM and PBO. From FIG. 2, it is apparent that the ratio between PBO and DM in terms of weight should be above 4, or rather above 5, in order to yield a high efficacy against mosquitoes. However, a ratio far above 5 does not improve the effect.

Examples of successful yarns had diameters of between 0.10 mm and 0.15 mm, for example around 0.12 mm, and a content of HDPE and LDPE in terms of weight at a ratio between 8 and 10, for example around 9, and containing 4 g DM per kg polymer and 25 g PBO per kg polymer. Due to necessary initial migration before a sufficient content is reached at the surface of the matrix, the yarn had to be stored for a certain time to reach sufficient efficacy, for example a week to reach 80% efficacy.

The content of DM and PBO may be varied. For example, in the yarn with a thickness of between 0.10 mm and 0.15 mm, and a HDPE and LDPE weight content ratio of between 8 and 10, the content of DM may be selected between 2 g and 6 g DM per kg polymer and correspondingly 4 to 10 times as much PBO, preferably between 5 and 7 times as much PBO, for example 6 times as much PBO.

The monofilament polyethylene yarns may successfully be used for bed nets, where the entire net is provided with such material. However, in case that the side walls of the nets are preferred to be produced in polyester multifilament due to the relatively higher softness and cotton like feeling, the extruded HDPE/LDPE monofilament yarn may be used for the top part of the net. The efficacy will in most cases still be high, because mosquitoes typically attack their potential victims from above and tend to land on the roof of bed nets, especially rectangular bed nets.

As a further addition, migration promoters may be included in the molten matrix prior to extrusion of the insecticidal polyethylene blend.

Figure 3:
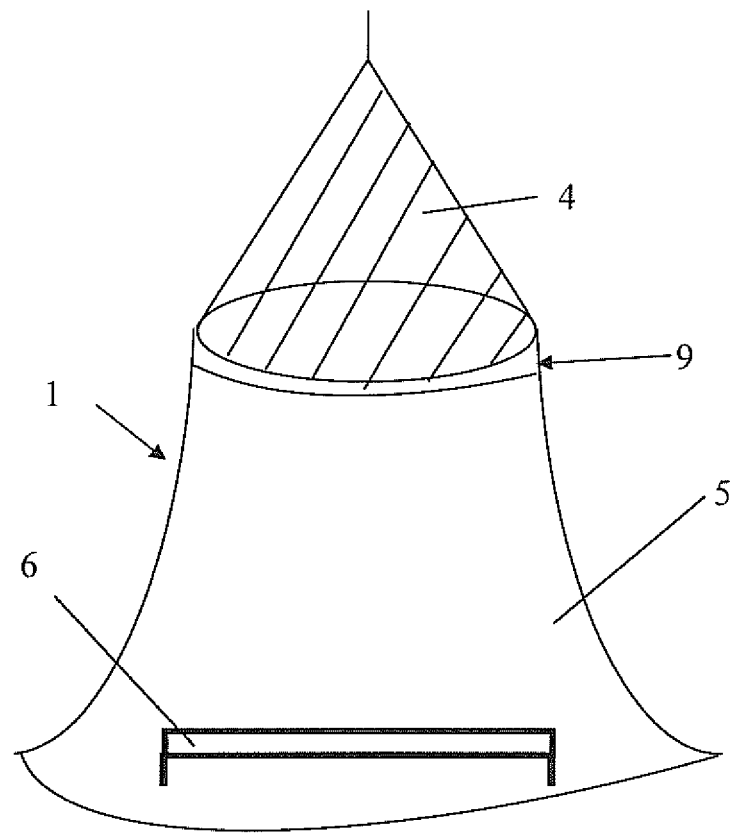
FIG. 3 shows a first embodiment of a bed net according to the invention with a roof that contains PBO and DM.

FIG. 3 illustrates a conical canopy net 1 above a bed 6 to protect humans on the bed 6 from being attacked by insects, primarily mosquitoes. The roof 4 of the net 1 is provided as a material according to the invention with PBO and DM incorporated in a polymer matrix, and the side walls 5 of the canopy 1 comprise an insecticide but no PBO. A stabilising ring 9 is inserted between the roof 4 and the side walls 5.

Figure 4:
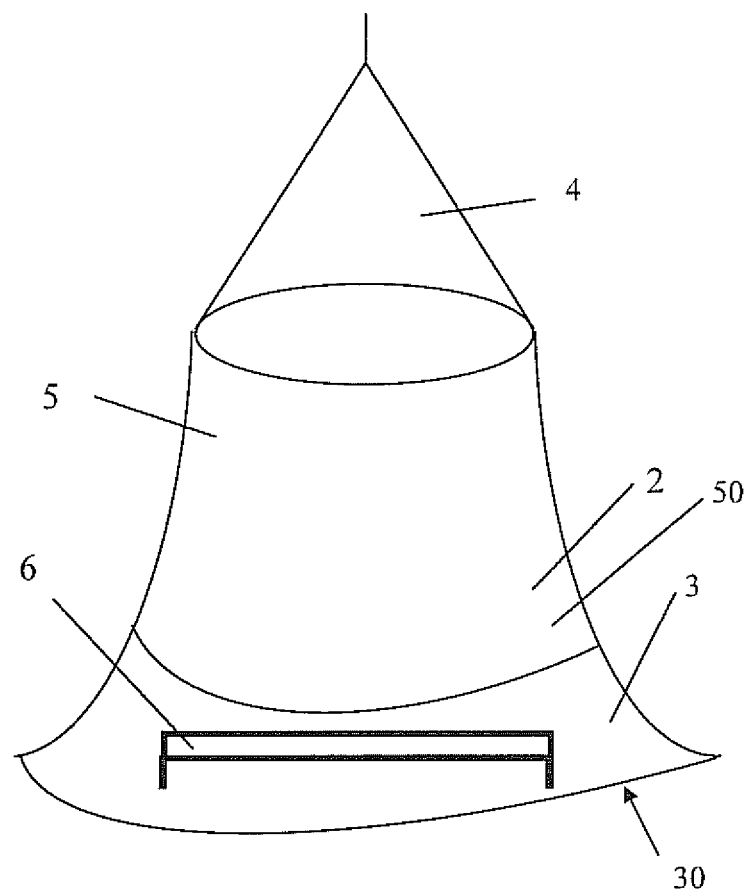
FIG. 4 shows a second embodiment of a bed net according to the invention, the bed net having a skirt.

FIG. 4 illustrates a conical canopy insecticidal barrier according to another embodiment of the invention, wherein the roof 4 and the side wall 5 are provided as a material according to the invention with PBO and DM incorporated in a polymer matrix. The side wall 5 extends to the lower edge 30 of the barrier and has an upper part 2 and a lower part 3. The canopy insecticidal barrier is intended to cover a space for human beings or animals, for example a bed 6 as illustrated in FIG. 4. In order to enter the space underneath the canopy, the lower part 3 of the barrier 1 is exposed to surface touch and, therefore, exposed to abrasion of insecticide from the surface of the material. In order to increase the strength of the net, the lower part 3 is has a material with higher abrasion resistance and mechanical strength, for example a stronger net, a fabric or a tarpaulin or a combination of these. Also, the lower part 3 may be provided with higher insecticidal content in order to take into account the higher abrasion of the insecticide from the surface of the material.

The thickness of the filaments for bed nets may vary in dependency of the actual requirements for the net. Typically, yarns with a weight of between 50 Denier and 100 Denier are used.

Figure 5:
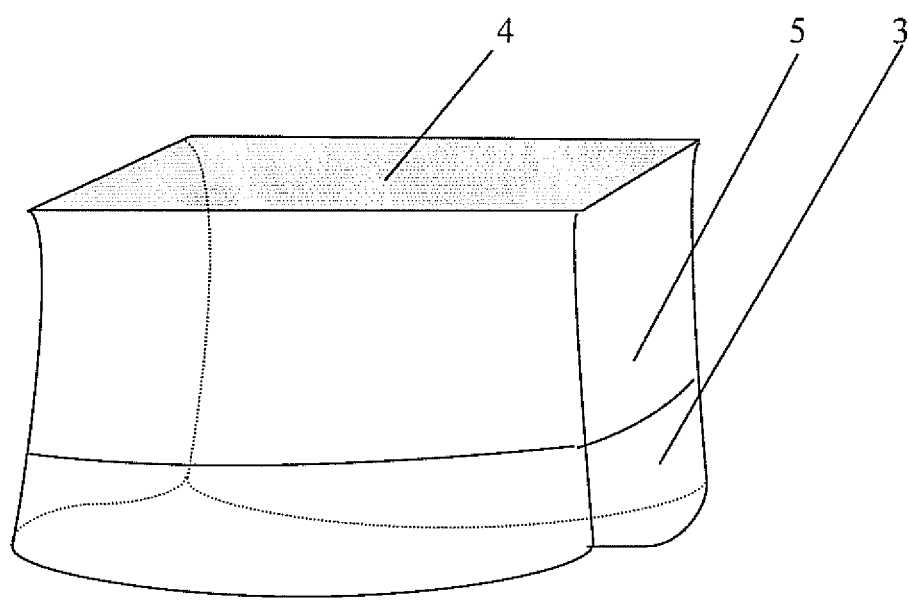
FIG. 5 illustrates a rectangular net.

FIG. 5 shows a rectangular shape for a net, which may substitute the shapes of the nets in FIG. 4 and FIG. 3. However, the net in FIG. 5 has a roof 4 with a polymer matrix according to the invention, whereas the side walls 5 are multifilament polyester in order for the side walls to have soft, cotton like feeling. In order to provide additional strength to the lower part 3 of the side walls 5, the net has a tighter knit in this part 3. The walls of the net are provided without PBO but with DM impregnation complying with WHO specification 333/TC and being wash resistant and largely in line with the impregnation method in the disclosure of International patent application WO 01/37662, which also is used for the well known bed net under the trademark PermaNet®. The side wall 5 is provided with between 2.5 g and 3.5 g DM per kg of the matrix, which mainly is the polymer. As the yarn density is different in the lower part 3 of the side walls 5, the amount per square meter is higher. For example, if the value is chosen to 2.8 g/kg in a 75 Denier yarn, for example with about 40 g/m² for the lower part of the side walls and 30 g/m² for the remaining part of the side walls, the DM level is 115 mg/m² of the lower part 3 of the side wall 5 and 85 mg/m² in the remaining part of the side wall 5. The preferred net had a minimum of 24 holes per cm². The preferred amount of DM in the roof net with 100 Denier was chosen to be between 3 and 5 g/kg cooperating with a PBO content between 5 to 7 times, rather around 6 times, as large as the DM content.

The invention claimed is:

1. An insecticidal polymer matrix comprising Piperonyl Butoxide (PBO) and deltamethrin (DM) which is incorporated within the cross-section of said matrix for later migration onto the surface of said matrix, wherein the ratio between the content of PBO and the content of DM in terms of weight is higher than 3, wherein the amount of DM in the polymer is between 1 g and 6 g per kg polymer, and wherein the insecticidal matrix is in the form of an extruded monofilament yarn comprising PBO and DM as part of a roof of a bed net and in the form of monofilament yarn containing DM but no PBO as side walls for the bed net.

2. An insecticidal polymer matrix according to claim 1, wherein the ratio between the content of PBO and the content of DM is higher than 5.

3. An insecticidal polymer matrix according to claim 2, wherein the ratio between the content of PBO and the content of DM is between 5 and 10.

4. An insecticidal polymer matrix according to claim 1, wherein the polymer is a thermoplastic polymer.

5. An insecticidal polymer matrix according to claim 4, wherein the polymer is a polyolefin.

6. An insecticidal polymer matrix according to claim 5, wherein the polymer is polyethylene.

7. An insecticidal polymer matrix according to claim 6, wherein the polyethylene comprises High Density Polyethylene (HDPE) and Low Density Polyethylene (LDPE), wherein the ratio of the contents of HDPE to LDPE in terms of weight is between 3 and 30.

8. An insecticidal polymer matrix according to claim 7, wherein the ratio of the contents of HDPE to LDPE is between 5 and 20.

9. An insecticidal polymer matrix according to claim 8, wherein the ratio of the contents of HDPE to LDPE is between 5 and 11.

10. An insecticidal polymer matrix according to claim 9, wherein the ratio of the contents of HDPE to LDPE is between 8 and 10.

11. An insecticidal matrix according to claim 1, wherein the insecticidal matrix is in the form of a monofilament with a diameter of between 0.05 mm and 0.35 mm.

12. An insecticidal matrix according to claim 9, wherein the diameter is between 0.1 mm and 0.15 mm.

13. An insecticidal matrix according to claim 10, wherein the content of DM is between 2 g and 6 per kg polymer.

14. An insecticidal matrix according to claim 7, wherein the insecticidal matrix is in the form of a monofilament with a diameter of between 0.05 mm and 0.35 mm, the weight content of DM is between 2 g and 6 g per kg polymer, the ratio between the content of HDPE relative to the content of LDPE in the matrix is between 5 and 20.

15. An insecticidal matrix according to claim 7, wherein the insecticidal matrix is in the form of a monofilament with a diameter of between 0.10 mm and 0.15 mm, the ratio between the content of HDPE relative to the content of LDPE in the matrix is between 8 and 10, the weight content of DM is between 3 g and 5 g per kg polymer, the weight content of PBO is between 5 and 7 times the weight content of the DM.

16. An insecticidal matrix according to claim 7, where the content of LDPE is between 9% and 11% of the weight of the matrix.

* * * * *